United States Patent
Smejkal

(10) Patent No.: US 9,120,759 B2
(45) Date of Patent: Sep. 1, 2015

(54) PROCESS FOR THE STEREOSELECTIVE PREPARATION OF A PYRAZOLE CARBOXAMIDE

(71) Applicant: Syngenta Participations AG, Basel (CH)

(72) Inventor: Tomas Smejkal, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/373,439

(22) PCT Filed: Feb. 13, 2013

(86) PCT No.: PCT/EP2013/052803
§ 371 (c)(1),
(2) Date: Jul. 21, 2014

(87) PCT Pub. No.: WO2013/120860
PCT Pub. Date: Aug. 22, 2013

(65) Prior Publication Data
US 2014/0364622 A1    Dec. 11, 2014

(30) Foreign Application Priority Data

Feb. 15, 2012  (EP) ..................... 12155526
Jun. 26, 2012  (EP) ..................... 12173642
Jul. 24, 2012  (EP) ..................... 12177606
Sep. 3, 2012  (EP) ..................... 12182799

(51) Int. Cl.
C07D 231/14   (2006.01)
C07C 45/61    (2006.01)
C07C 49/573   (2006.01)
C07C 249/08   (2006.01)
C07C 251/32   (2006.01)
C07C 251/66   (2006.01)

(52) U.S. Cl.
CPC .............. *C07D 231/14* (2013.01); *C07C 45/61* (2013.01); *C07C 49/573* (2013.01); *C07C 249/08* (2013.01); *C07C 251/32* (2013.01); *C07C 251/66* (2013.01)

(58) Field of Classification Search
None
See application file for complete search history.

(56) References Cited

FOREIGN PATENT DOCUMENTS

WO    2010049228    5/2010
WO    2011015416    2/2011
WO    2012101139    8/2012

OTHER PUBLICATIONS

International Search Report dated Mar. 13, 2013 for International Patent Application No. PCT/EP2013/052803.

*Primary Examiner* — Samantha Shterengarts
(74) *Attorney, Agent, or Firm* — R. Kody Jones

(57) ABSTRACT

The present invention relates to a process for the enantioselective preparation of 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide of formula Ib.

13 Claims, No Drawings

PROCESS FOR THE STEREOSELECTIVE PREPARATION OF A PYRAZOLE CARBOXAMIDE

This application is a 371 of International Application No. PCT/EP2013/052803, filed Feb. 13, 2013, which claims priority to EP Patent Application No. 12155526.2, filed Feb. 15, 2012; EP Patent Application No. 12173642.5, filed Jun. 26, 2012; EP Patent Application No. 12177606.6; and EP Patent Application No. 12182799.2 filed Sep. 3, 2012, the contents of which are incorporated herein by reference herein.

The present invention relates to a process for the stereoselective (enantioselective) preparation of 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide.

The compound 3-difluoromethyl-1-methyl-1H-pyrazole-4-carboxylic acid (9-dichloromethylene-1,2,3,4-tetrahydro-1,4-methano-naphthalen-5-yl)-amide is described for example in WO 2007/048556. Said compound shows an excellent fungicidal activity and is for example effective for the reduction of mycotoxin contamination in plants. Mycotoxins (aflatoxins, ochratoxins, patulin, fumonisins, zearalenones, trichothecenes, in particular deoxynivalenol) are produced for example by different *Fusarium* and *Aspergillus*, *Penicillium* and *Alternaria* species as described in WO 2012/072575.

Said compound can occur in two enantiomeric forms, Ia

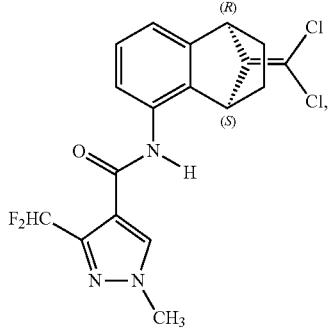

(Ia)

which chemical designation is 3-difluoromethyl-1-methyl-1H-pyrazole-4-carboxylic acid ((1R,4S)-9-dichloromethylene-1,2,3,4-tetrahydro-1,4-methano-naphthalen-5-yl)-amide, and Ib

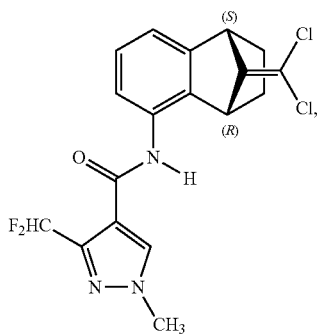

(Ib)

which chemical designation is 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide.

The enantiomer of formula Ib shows a more prominent fungicidal activity. A fungicide with an excess of the fungicidally more active enantiomer can be applied in lower concentrations with the same efficiency as the racemate which is economically advantageous. It is therefore highly desired to selectively prepare the Ib-enantiomer of said compound.

It is known from WO 2011/015416 to prepare the racemic form of 3-dichloromethyl-1-methyl-1H-pyrazole-4-carboxylic acid (9-dichloromethylene-1,2,3,4-tetrahydro-1,4-methano-naphthalen-5-yl)-amide by a) reducing the compound of formula II

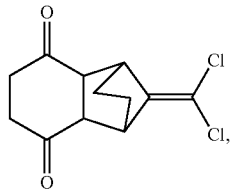

(II)

in the presence of a reducing agent to the compound of formula III

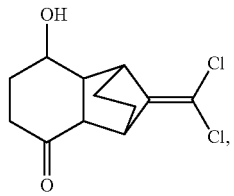

(III)

b) dehydrating the compound of formula III in the presence of an acid to the compound of formula IV

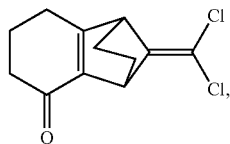

(IV)

c) reacting the compound of formula IV with hydroxylamine to the compound of formula V

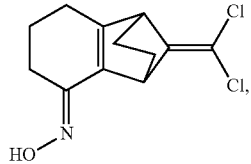

(V)

and d) acylating the oxime oxygen of the compound of formula V in the presence of a solvent and an acylating agent and finally reacting the obtained product with the compound of formula VI

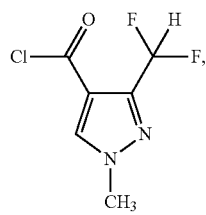

(VI)

or e) reacting the compound of formula V with an excess of the compound of formula VI. The product of this process is 3-difluoromethyl-1-methyl-1H-pyrazole-4-carboxylic acid (9-dichloromethylene-1,2,3,4-tetrahydro-1,4-methano-naphthalen-5-yl)-amide in form of the racemate.

The two enantiomers of 3-difluoromethyl-1-methyl-1H-pyrazole-4-carboxylic acid (9-dichloromethylene-1,2,3,4-tetrahydro-1,4-methano-naphthalen-5-yl)-amide can be separated for example by chiral chromatography of the racemate. However, said method is expensive and unsuitable for large-scale production of said compound.

The compound of formula III was prepared according to WO 2011/015416 in racemic form as a mixture of isomers as shown below as compounds IIIa, IIIb, IIIc and IIId:

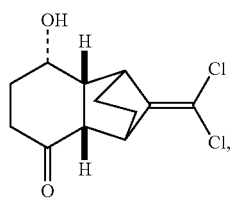

(IIIa)

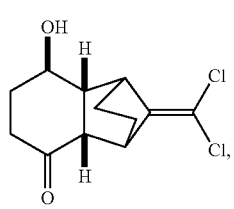

(IIIb)

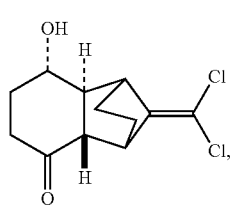

(IIIc)

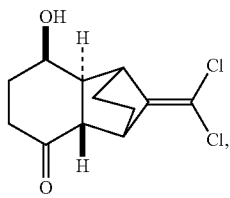

(IIId)

It has surprisingly been found that the 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide (enantiomer of formula Ib) can be produced by this process in excess to 3-difluoromethyl-1-methyl-1H-pyrazole-4-carboxylic acid ((1R,4S)-9-dichloromethylene-1,2,3,4-tetrahydro-1,4-methano-naphthalen-5-yl)-amide (enantiomer of formula Ia) if the enantioselective step is the enantioselective synthesis of the compound of formula III, so that the enantiomer (1S,4R)-9-dichloromethylene-8-hydroxy-octahydro-1,4-methano-naphthalen-5-one of formula IIIe

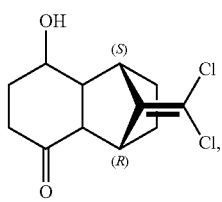

(IIIe)

is obtained in excess. The enantioselective synthesis of the compound of formula III allows a very cost effective preparation of the fungicide 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide with high yields.

The compound of formula IIIe can occur in form of the following isomers of formulae IIIf-IIIm:

(IIIf)

(IIIg)

-continued (IIIh)
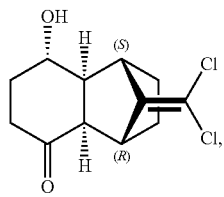

(IIIi)
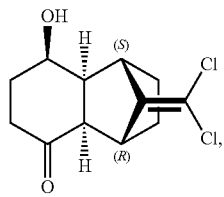

(IIIj)
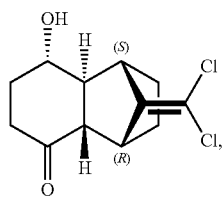

(IIIk)
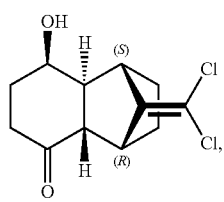

(IIIL)
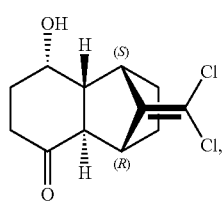

(IIIm)
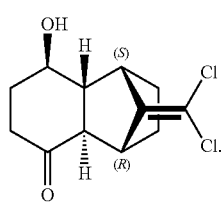

This invention encompasses the preparation of all isomers of formula IIIe.

It has further been found that the 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide (enantiomer of formula Ib) can be produced in higher yields if the compound of formula IIIe can be prepared selectively in form of its isomer of formula IIIf. The preparation of the compound of formula IIIf in enantiomerically enriched form, i.e. in an excess to the isomers of formulae IIIg-IIIm, allows a higher yield in the dehydration step, which results in a higher yield of enantiomer of formula Ib.

The aim of the present invention is therefore to provide a novel process for the enantioselective preparation of 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide of formula Ib (Ib)
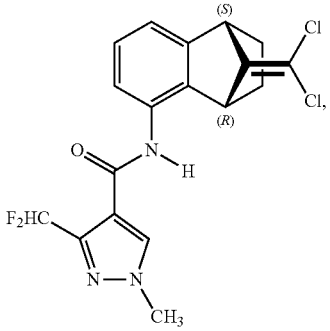

which process comprises a) reducing a compound of formula II (II)
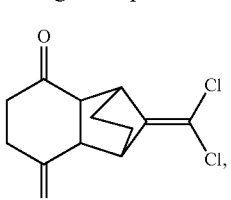

with an enantioselective reagent to a compound of formula IIIe (IIIe)
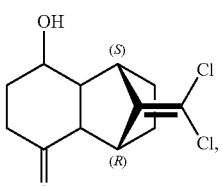

b) dehydrating the compound of formula IIIe in the presence of an acid to the compound of formula IVa (IVa)
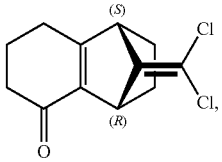

c) reacting the compound of formula IVa with hydroxylamine to the compound of formula Va (Va)
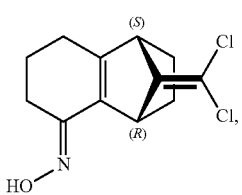

and d) acylating the oxime oxygen of the compound of formula Va in the presence of a solvent and an acylating agent and finally reacting the obtained product with the compound of formula VI

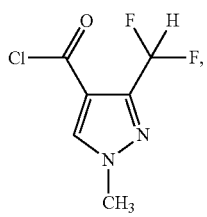
(VI)

or e) reacting the compound of formula V with an excess of the compound of formula VI.

The product of this process is 3-difluoromethyl-1-methyl-1H-pyrazole-4-carboxylic acid (9-dichloromethylene-1,2,3,4-tetrahydro-1,4-methano-naphthalen-5-yl)-amide I in form of a mixture of formula Ia and Ib, wherein 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide (Ib) is present in the mixture in an excess of 55-99% to the compound of formula Ia.

The alkyl groups occurring in the definitions of the substituents can be straight-chain or branched and are, for example, methyl, ethyl, n-propyl, n-butyl, n-pentyl, n-hexyl, iso-propyl, sec-butyl, iso-butyl or tert-butyl.

The alkoxy groups occurring in the definitions of the substituents can be straight-chain or branched and are, for example, methoxy, ethoxy, n-propoxy, n-butoxy, n-pentoxy, n-hexyloxy, iso-propoxy, n-butoxy, sec-butoxy, iso-butoxy or tert-butoxy.

According to the present invention, preparation in enantiomerically enriched form or in excess means that the molar proportion of the desired product (formula IIIe, formula IIIf and formula Ib) is greater than 50% (for example greater than 55, 60, 65, 70, 75, 80, 85, 90, 95, 96, 97, 98 or 99%) of the total amount of all isomers present in the reaction mixture.

Reaction Step a):

The reduction of carbonyl compounds to alcohols is a reaction of considerable practical interest. From both economical and ecological point of view, catalytic methods are more beneficial than stoichiometric reduction systems. Good results have been obtained using catalytic systems based on transition metals e.g. Ir, Rh, Pd, Ni and Ru. In addition, with a suitable chiral catalyst, enantioselective hydrogenation of carbonyl compounds can be achieved with the formation of optically active alcohols with high enantiomeric excesses. (Catalytic asymmetric synthesis, Iwao Ojima, third Edition, Wiley-VCH 2010, pp 384-413 and the literature cited therein.) In this respect, ruthenium derivatives of the type [Ru(phosphine or diphosphine)~(amine or diamine)] in a basic environment have been shown as excellent catalysts for the selective hydrogenation, in homogeneous phase, of varying types of ketones. The reactions are generally conducted with hydrogen under pressure at moderate temperatures. (R. Noyori, T. Ohkuma, Angew. Chem. Int. Ed. Engl. 2001, 40, 40-73)

As an alternative, catalytic reduction methods based on hydrogen transfer reactions have also been established. In these processes 2-propanol or formic acid is normally used as hydrogen source. In this respect, ruthenium derivatives of the type [Ru(arene)~(diamine derivative)] but also rhodium and iridium derivatives have been shown as excellent catalysts for the selective hydrogenation, in homogeneous phase, of varying types of ketones. (T. Ikariya, A. J. Blacker, Acc. Chem. Res. 2007, 40, 1300-1308)

Regarding both hydrogenation and transfer hydrogenation, it has been found however, that one specific catalyst or a class of catalysts cannot be used equally well in all hydrogenations, but that each reduction problem has to be investigated separately with regard to the catalyst use and the conditions. This is all the more so in the case of hydrogenations that take place with catalysts that consist not only of a ligand and a transition metal but that, as outlined in the above cases, require two different ligands and the transition metal in order to be sufficiently active.

Meso-diketones of Formula VII

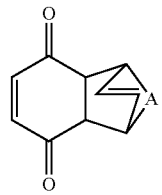
(VII)

wherein A is a methylene group which can be substituted, for example, A is the group

wherein $R^1$ and $R^2$ are each, independently from each other, hydrogen, halo, $C_1$-$C_4$alkyl, $C_1$-$C_4$alkoxy, $C_1$-$C_4$haloalkyl or $C_1$-$C_4$haloalkoxy; or A is the group

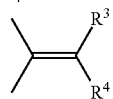

wherein $R^3$ and $R^4$ are each, independently, hydrogen, halo, $C_1$-$C_4$alkyl, $C_1$-$C_4$alkoxy, $C_1$-$C_4$haloalkyl or $C_1$-$C_4$haloalkoxy; are easily prepared from Diels-Alder adducts of p-benzoquinone and optionally substituted cyclopentadiene, optionally followed by reduction of double bonds.

In contrast to the readily synthetic availability, there have been only few studies toward an enantioselective desymmetrizing reduction of the compound of formula VII. S. Bräse and coworkers (C. F. Nising, U. K. Ohnemüller, S. Bräse, Synthesis 2006, 16, 2643-2645) reported on an ennatioselective desymetrization of the compound of formula VIIa using Corey-Bakshi-Shibata (CBS)-reduction, but the low temperature (−30 to −78° C.) and high cost of catecholborane reagent limit its practical use.

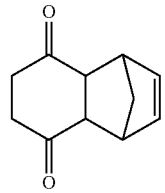
(VIIa)

Marchand and co-workers (Marchand, A. P.; Xing, D.; Wang, Y.; Bott, S. G. Tetrahedron: Asymmetry 1995, 6, 2709-2714) developed asymmetric reduction of the compound of formula VIIa utilising Baker's yeast, but extremely long reaction times (60 h), low yield and low volume yield make this method unsuitable for scale up. It should be also noted that these catalysts do not in general allow access to both enantiomers.

Noyori and co-workers (S. Hashiguchi, A. Fujii, J. K. Haack, K. Matsumura, T. Ikariya, R. Noyori, Angew. Chem. Int. Ed. Engl. 1997, 36, 288-290) reported on an enantioselective synthesis if hydroxyketone (VIII) via Ru-catalysed hydrogen transfer but only in the direction of oxidation (starting from the corresponding meso-diol).

(VIII)

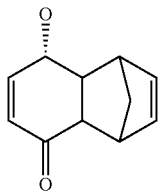

In the abstract: "This method provides access to alcohols that are not available from the corresponding ketones by standard enantioselective reduction."

and in the text regarding enantioselective reduction of prochiral ketones using 2-propanol as a hydrogen source " . . . high enantioselectivity is not possible in the preparation of alcohols having a high reduction potential such as 2,3-benzo-2-cyclenols and 1-phenylethanols with an electron-donating group on the aromatic ring."

McIntosh and co-workers (D. R. Clay, A. G. Rosenberg, M. C. McIntosh, Tetrahedron: Asymmetry 2011, 22, 713-716.) reported on an enantioselective and diastereoselective transfer hydrogenation (no hydrogenation reported) of tetracyclic epoxy diketone (XX). However, person skilled in the art would immediately recognise that the α,β-epoxy ring brings about an alteration of the steric and electronic properties of the carbonyl moiety. Therefore, it could not be expected that a tricyclic compound without the epoxy ring would react analogously in a stereoselective way.

(XX)

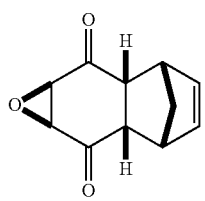

Therefore, in the light of the teaching of the references mentioned above, a person skilled in the art could not expect the stereoselective reduction of a compound of formula II via hydrogenation or transfer hydrogenation to proceed with high enantioselectivity and/or diastereoselectivity.

Preferred enantioselective reagents are ruthenium complexes selected from the following group consisting of the compounds of formulae IX to XIV:

(IX)

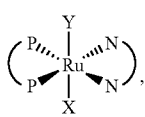

(X)

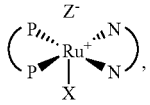

(XI)

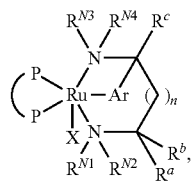

(XII)

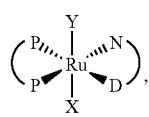

(XIII)

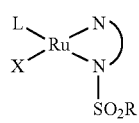

(XIV)

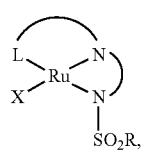

wherein

X and Y are equal or different and represent a halogen, hydrogen, or an anionic group, for example $BH_4^-$;

Z represents an anion, for example $BF_4^-$, $[B(C_6F_5)_4]^-$, $TfO^-$, $ClO_4^-$, $SbF_6^-$ or $PF_6^-$, L represents an aryl, in particular a phenyl group, which can be substituted by $C_1$-$C_4$alkyl, $C_1$-$C_4$alkoxy or trialkylsilyl. Specific examples include, but are not limited to benzene, p-cymene, mesitylene and hexamethylbenzene.

The catalysts according to the invention must be chiral. For example, non-chiral catalysts like $RuCl_2(PPh_3)_2(en)$ (described for example in JP 11189600A2 and CN1680412, CAS Number 212210-86-1 or 83438-00-0)

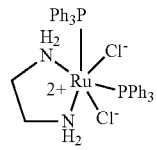

$RuCl_2(PPh_3)_2(en)$, $RuCl_2(PPh_3)_2(pica)$ (described for example, in WO 2005/105819, CAS Number 850346-91-7 or 850424-31-6)

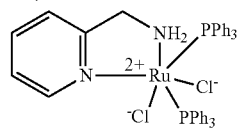

$RuCL_2(PPh_3)_2(pica)$ and the catalyst

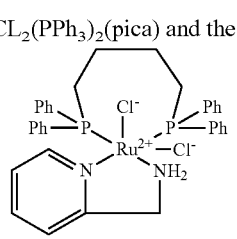

(CAS Number 850424-32-7, 850346-92-8 and 850424-33-8) lead to racemic products.

The Group of Formula (XV)

(XV)

represents in the compounds of formulae IX-XII a phosphorus-containing ligand, preferably a chiral phosphorus-containing ligand, more preferably a chiral biphosphine or biphosphite, or their mixed forms. Chiral phosporus-contaning ligands are known in the art and may used in the present invention, examples are given in "Catalytic asymmetric synthesis", Iwao Ojima, third Edition, Wiley-VCH 2010, pp 344-357 and the literature cited therein; and in STREM catalog of phosphorus ligands and compounds:
http://www.strem.com/uploads/resources/documents/phosphorusligands.pdf Preferred diphosphine ligands represented by formula (XV) of the invention are selected from the group consisting of
2,2'-bis(diphenylphosphino-1,1'-binaphtyl(binap);
2,2'-bis[di(p-tolyl)phosphino]-1,1'-binaphthyl(tolbinap);
2,2'-bis[di(3,5-xylyl)phosphino]-1,1'-binaphthyl(xylbinap);
2,2'-bis[di(p-t-butylphenyl)phosphino]-1,1'-binaphthyl;
2,2'-bis[di(p-methoxyphenyl)phosphino]-1,1'-binaphthyl;
2,2'-bis(diphenylphosphino)-5,5',6,6',7,7',8,8'-octahydro-1,1'-binaphthyl;
2,2'-bis(di-p-tolylphosphino)-5,5',6,6',7,7',8,8'-octahydro-1,1'-binaphthyl;
2,2'-bis(di-3,5-xylyl phosphino)-5,5',6,6',7,7',8,8'-octahydro-1,1'-binaphthyl(xylyl-H8-binap);
((4,4'-bi-1,3-benzodioxol)-5,5'-diyl)bis(diphenylphosphine) (segphos);
(4,4'-bi-1,3-benzodioxol)-5,5'-diyl)bis(di(3,5-xylyl)phosphine) (dm-segphos);
(4,4'-bi-1,3-benzodioxol)-5,5'-diyl)bis(di(3,5-di-t-butyl-4-methoxyphenyl)phosphine);
2,2'-bis(diphenylphosphino)-6,6'-dimethoxy-1,1'-biphenyl (MeO-biphep);
2,2'-bis(di-p-tolylphosphino)-6,6'-dimethoxy-1,1'-biphenyl (tolyl-MeO-biphep);
2,2'-bis(di-3,5-xylylphosphino)-6,6'-dimethoxy-1,1'-biphenyl (xylyl-MeO-biphep);
2,2'-bis(diphenylphosphino)-6,6'-dimethyl-1,1'-biphenyl;
2,2'-bis(di-o-tolylphosphino)-6,6'-dimethyl-1,1'-biphenyl;
2,2'-bis(di-m-fluorophenylphosphino)-6,6'-dimethyl-1,1'-biphenyl;
2,2',6,6'-tetramethoxy-4,4'-bis(diphenylphosphino)-3,3'-bipyridine (p-phos);
2,2',6,6'-tetramethoxy-4,4'-bis(di-p-tolylphosphino)-3,3'-bipyridine (p-tolyl-p-phos);
2,2',6,6'-tetramethoxy-4,4'-bis(di-o-tolylphosphino)-3,3'-bipyridine (o-tolyl-p-phos);
2,2',6,6'-tetramethoxy-4,4'-bis(di-3,5-xylylphosphino)-3,3'-bipyridine (xylyl-p-phos);
4,12-bis(di-3,5-xylylphosphino)[2.2]-paracyclophane;
4,12-bis(diphenylphosphino)[2.2]-paracyclophane;
4,12-bis(di-p-tolylphosphino)[2.2]-paracyclophane;
4,12-bis(di-o-tolylphosphino)[2.2]-paracyclophane;
N,N-dimethyl-1-[1',2-bis(diphenylphosphino)ferrocenyl]ethylamine;
2,3-bis(diphenylphosphino)butane (chiraphos);
1-cyclohexyl-1,2-bis(bisdiphenylphosphino)ethane;
2,3-0-isopropylidene-2,3-dihydroxy-1,4-bis(diphenylphosphino)butane;
1,2-bis[(o-methoxyphenyl)phenylphosphino]ethane (dipamp);
1,2-bis(2,5-dimethylphosphorano)ethane;
N,N'-bis(diphenylphosphino)-N,N'-bis(I-phenylethyl)ethylenedamine;
1,2-bis(diphenylphosphino)propane (prophos);
2,4-bis(diphenylphosphino)pentane;
cyclohexylanisylmethylphosphine;
2,3-bis(diphenylphosphino)-5-norbornene;
3,4-bis(diphenylphosphino)-1-benzylpyrrolidine;
1-[1',2-bis(diphenylphosphino)ferrocenyl]ethyl alcohol;
4,5-bis(diphenylphosphinomethyl)-2,2-dimethyl-1,3-dioxolan (diop);
4-(i-propyl)-2-{(S)-2-(diphenylphosphino)ferrocenyl}oxazoline;
3,4-bis(diphenylphosphino)-1-benzylpyrrolidine (deguphos),
2,3-bis(diphenylphosphino)-bicyclo[2.2.1]hepto-5-ene (NORPHOS);
I-tertiary-butoxycarbonyl-4-diphenylphosphino-2-(diphenylphosphinomethyl)pyrrolidine (BPPM);
2,3-bis(tertiary-butylmethylphosphino) quinoxaline (QuinoxP*);
2,4-bis(diphenylphosphino)pentane (SKEWPHOS);
2,4-bis(di(3,5-xylyl)phosphino)pentane (XyISKEWPHOS);
4,4'-bis(diphenylphosphino)-2,2',5,5'-tetramethyl-3,3'-bithiophene (TMBTP); xylyl-C3-tunephos;
xylyl-synphos; Josiphos type ligands; Garphos type ligands; Deguphos; PhanePHOS; BDPP; Norphos; ProPhos;
1,1'-bis(diphenylphosphino)ferrocene (DPPF);
bis(2-diphenylphosphinophenyl) ether (DPEphos); bis (diphenylphosphino)methane;
1,2-bis(diphenylphosphino)ethane; 1,3-bis(diphenylphosphino)propane; and 1,4-bis(diphenylphosphino)butane; 1,5-bis(diphenylphosphino)pentane.

The diphosphine as specifically exemplified in the above may be an optically active diphosphine.

The Group of Formula

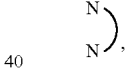
(XVI)

represents in the compounds of formulae IX-X an amino group-containing ligand, preferably a chiral amino group-containing ligand, more preferably a chiral diamine ligand. Chiral amino group-containing ligands are known in the art and may used in the present invention, examples are given in R. Noyor, T. Ohkuma, Angew. Chem., Int. Ed. Engl. 2001, 40, 40-73; in WO2004/007506 and in STREM catalog of other ligands: http://www.strem.com/uploads/resources/documents/other_ligands.pdf Specific examples of the diamine ligands represented by formula (XVI) of the invention include
1,2-diphenylethylenediamine (DPEN);
1,2-bis(naphthyl)ethylenediamine;
1,1-bis(4-methoxyphenyl)-3-methyl-1,2-butanediamine (DAIPEN);
1,2-bis(2-methoxyphenyl)ethane-1,2-diamine;
spiro[4.4]nonane-1,6-diamine;
1-pyrrolidinecarboxylic acid, 4-amino-2-(aminomethyl)-1,1-dimethylethyl ester;
1,3-diphenyl-1,3-propanediamine;
1,4-diphenyl-1,4-butanediamine;
1-phenyl-1,2-ethanediamine;
2-pyrrolidinemethanamine;
3,4-O-isopropylidenehexane-2,5-diamine (IPHAN);
2,3-O-isopropylidenebutane-1,4-diamine (IPBAN);
1,2-cyclohexanediamine (DACH);

1,2-ethanediamine (en);
1,2-propanediamine;
2,4-pentanediamine;
2,5-hexanediamine;
1,2-benzenediamine;
N1,N2-dimethyl-1,2-ethanediamine and
DMDPEN.

The diamine ligands as specifically exemplified in the above may be optically active.

The Group of Formula

     (XVII)

represents in the compound of formula XII a amino group-containing ligand with a second donor group, D is preferably representing a nitrogen, sulphur or phosphorus. XVII is optionally a chiral ligand.

A range of chiral amino group-containing ligands is known and may used in the present invention, examples are given in STREM catalog of other ligands: http://www.strem.com/uploads/resources/documents/other_ligands.pdf Specific examples of the amino group-containing ligands represented by formula (XVII) of the invention include
2-(α-methylmethanamine)-1H-benzimidazole (Me-BI-MAH);
2-(α-(i-propyl)methanamine)-1H-benzimidazole (i-Pr-BI-MAH);
2-(α-(i-butyl)methanamine)-1H-benzimidazole (i-Bu-BI-MAH);
2-(α-(t-butyl) methanamine)-1H-benzimidazole (t-Bu-BI-MAH);
2-(di-i-propylphosphino)ethanamine;
2-(diphenylphosphino)ethylamine;
2-Pyridinemethanamine (PICA);
1-(2-pyridyl)ethanamine;
2-(diphenylphosphino)-1,2-diphenylethanamine;
2-amino-1-phenylpropyldiphenylphosphine and
3-(diphenylphosphino]propylamine.

The ligands as specifically exemplified in the above may be optically active.

The Group of Formula

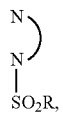     (XVIII)

represents in the compound of formula XIII a amino sulfonamide ligand, more preferably a chiral amino sulfonamide ligand. A range of chiral amino sulfonamide ligands is known and may used in the present invention, examples are given in T. Ikariya, A. J. Blacker, Acc. Chem. Res. 2007, 40, 1300-1308.

Specific examples of the amino sulfonamide ligand represented by the compound of formula XVIII comprise
N-(4-toluenesulfonyl)-1,2-diphenylethylenediamine (TsDPEN);
N-(methanesulfonyl)-1,2-diphenylethylenediamine (MsDPEN) and
N-pentafluorophenylsulfonyl-1,2-diphenylethylenediamine (FsDPEN).

The Group of Formula

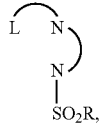     (XIX)

represents in the compound of formula XIV an aryl-amino-sulfonamide ligand, more preferably a chiral ligand containing L (definition above) and N∩N—SO$_2$R (VIII, definition above) which are connected by a C$_{1-6}$ bridge which may be optionally interrupted by a heteroatom.

A range of chiral aryl-amino-sulfonamide ligands is known and may used in the present invention, examples are given in T. Touge, T. Hakamata, H. Nara, T. Kobayashi, N. Sayo, T. Saito, Y. Kayaki, T. Ikariya J. Am. Chem. Soc. 2011, 133, 14960-14963 and in Hannedouche, J.; Clarkson, G. J.; Wills, M. J. Am. Chem. Soc. 2004, 126, 986-987.

Specific examples of the aryl-amino-sulfonamide ligand represented by formula (XIX) of the invention comprise
N-[2-(phenethyloxymethylamino)-1,2-diphenyl-ethyl]benzenesulfonamide;
N-[1,2-diphenyl-2-(3-phenylpropylamino)ethyl]benzenesulfonamide and
N-[1,2-diphenyl-2-(4-phenylbutylamino)ethyl]enzenesulfonamide.

The ligands as specifically exemplified in the above may be optically active.

The Group of Formula

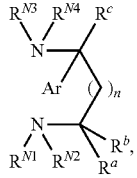     (XXI)

represents in the compound of formula XI a tridentate diamine ligand, more preferably a chiral tridentate diamine ligand. $R^a$, $R^b$ and $R^c$ each independently represent a hydrogen atom, an optionally substituted $C_1$-$C_{20}$alkyl group, an optionally substituted $C_2$-$C_{20}$alkenyl group, an optionally substituted $C_3$-$C_8$ cycloalkyl group, an optionally substituted $C_7$-$C_{20}$ aralkyl group, an optionally substituted aryl group, or an optionally substituted heterocyclic group, and $R^b$ and $R^c$ may form an alkylene group or alkylenedioxy group; $R^{N1}$, $R^{N2}$, $R^{N3}$, and $R^{N4}$ each independently represent a hydrogen atom, an optionally substituted $C_1$-$C_{20}$ alkyl group, an optionally substituted $C_2$-$C_{20}$alkeny group, an optionally substituted $C_3$-$C_8$ cycloalkyl group, an optionally substituted $C_7$-$C_{20}$ aralkyl group, an optionally substituted $C_3$-$C_8$ cycloalkyl group, at least one of $R^{N1}$, $R^{N2}$, $R^{N3}$, and $R^{N4}$ represents a hydrogen atom, and $R^{N1}$ and $R^a$ may form an alkylene group; n represents an integer 0 to 3, and Ar represents an optionally substituted arylene group. Preferred optional substituents are described in WO 2011/135753. A range of suitable tridentate diamine ligands and the corresponding ruthenium complexes (XI) is known and may used in the present invention, examples are given in WO2011/135753.

A specific tridentate diamine ligand represented by formula (XXI) of the invention is 1-(4-methoxyphenyl)-1'-(4-methoxyphenyl-kC)-3-methyl-1,2-butanediamine.

Specific examples of ruthenium complexes represented by formula (IX) of the invention include:
RuCl$_2$[(R)-xylbinap][(R,R)-dpen] CAS=[220114-38-5]:
dichloro{(R)-(+)-2,2'-bis[di(3,5-xylyl)phosphino]-1,1'-binaphthyl0}[(1R,2R)-(+)-1,2-diphenylethylenediamine]ruthenium(II); and
RuCl$_2$[(R)-xylbinap][(R)-daipen] CAS=[220114-32-9]:
Dichloro{(R)-(+)-2,2'-bis[di(3,5-xylyl)phosphino]-1,1'-binaphthyl}[(2R)-(−)-1,1-bis(4-methoxyphenyl)-3-methyl-1,2-butanediamine]ruthenium(II);
RuCl$_2$[(R)-xylbinap][(R,R)-dpen, CAS=[220114-38-5]; and
RuCl$_2$[(R)-xyl-P-Phos][(R)-iphan], CAS=[832117-89-2].

A preferred example of ruthenium complexes represented by formula (XI) of the invention is
(R)-RUCY™-XylBINAP, Strem catalog 44-0217,
chloro{(R)-(+)-2,2'-bis[di(3,5-xylyl)phosphino]-1,1'-binaphthyl}[(2R)-(−)-1-(4-methoxyphenyl)-1'-(4-methoxyphenyl-kC)-3-methyl-1,2-butanediamine]ruthenium(II).

A preferred example of ruthenium complexes represented by formula (XII) of the invention is:
RuCl$_2$[(S,S)-DIOP](S)-Me-BIMAH (STREM catalog Nr.=44-0955)
Dichloro[(4S,5S)-(+)-4,5-bis(diphenylphosphinomethyl)-2,2-dimethyl-1,3-dioxolane][(S)-(−)-2-(α-methylmethanamine)-1H-benzimidazole]ruthenium(II).

An example of ruthenium complexes represented by formula (XIII) of the invention is
RuCl[(S,S)-Tsdpen](p-cymene) CAS=[192139-90-5],
chloro{[(1S,2S)-(+)-2-amino-1,2-diphenylethyl](4-toluenesulfonyl)amido}(p-cymene)ruthenium(II).

An example of ruthenium complexes represented by formula (XIV) of the invention is
(S,S)-Ts-DENEB™, CAS=[1384974-37-1], N-[(1S,2S)-1,2-diphenyl-2-(2-(4-methylbenzyloxy)ethylamino)-ethyl]-4-methylbenzene sulfonamide(chloro)ruthenium(II).

It is known to carry out enantioselective catalytic hydrogenations by two process variants that differ in principle (with molecular hydrogen or by transfer hydrogenation). Also, the process of the subject matter of the invention may be carried out either in the presence of molecular hydrogen or by means of transfer hydrogenation. Both types of process have been evaluated in the prior art and may be used analogously. (Catalytic asymmetric synthesis, Iwao Ojima, third Edition, Wiley-VCH 2010, pp 384-413)

It has been found that acid residues affect the present reaction in that on the one hand they lead to a low yield and on the other hand cause a low enantiomer enrichment of the products. Therefore, it has proved advantageous if a base is present in the reaction step a) according to the invention. Suitable bases are for example alkali metal alcoholates, such as for example sodium methanolate, sodium ethanolate or potassium tert.-butylate or potassium isopropylate or carbonates or hydroxides of alkali or alkaline earth metals. Also advantageous are organic nitrogen bases such as pyridine, DMAP, triethylamine, Hunig base, 1,2-ethylenediamine, diphenylenediamine, 1,2-di-(4-anisyl)-2-isobutyl-1,2-ethylenediamine and 1,2-di-(4-anisyl)-2-isopropyl-1,2-ethylenediamine. A particularly preferred base is potassium tert.-butylate.

A person skilled in the art is able to determine a suitably adequate excess of base. A molar excess of base referred to the catalyst used of between 1:1 and 1000:1 is advantageous, an excess of >10:1 being particularly preferred and an excess of >2:1 being most particularly preferred. One of the bases mentioned above is accordingly added to the substrate in an amount of 0.1-50 mol %, particularly preferably 0.1-10% and most particularly preferably 0.1-5% referred to the latter.

All inert solvents known to the person skilled in the art for this purpose may be used, also mixtures of these solvents in any composition may be used. Preferred classes of solvents include alcohols, ethers, esters, nitriles, amines, amides, hydrocarbons, aromatic hydrocarbons and chlorinated hydrocarbons. Particularly referred solvents and solvent mixture according to the invention include: methanol, ethanol, isopropanol, tert.-butanol, ethylacetate, isopropyl acetate, acetonitril, triethylamine, tetrahydrofurane, 2-methyl-tetrahydrofurane, tetrahydrofuran-2-ylmethanol, toluene, xylene, chlorobenzene, dimethylacetamide, dimethylformamide N-methyl-2-pyrrolidone.

The hydrogenation or transfer hydrogenation catalyst comprising is advantageously used in a concentration of 0.001-5 mol % referred to the substrate to be hydrogenated. It is particularly preferred to use the catalyst in, a concentration that is as low as possible while ensuring the optimum possible conversion rate. The catalyst is particularly preferably used in a concentration of 0.01-1 mol %.

The temperature during the hydrogenation or transfer hydrogenation reaction may in principle be chosen arbitrarily by the person skilled in the art as long as a sufficiently quick and selective reaction is achieved. The reaction is accordingly preferably carried out at temperatures between −10° and 100° C., more preferably between 0° and 80° C. and particularly preferably between 0° and 60° C.

Reaction time of hydrogenation or transfer hydrogenation is between 10 minutes and 48 hours, preferably between 30 minutes and 24 hours, most preferably between 1 hour and 12 hours.

Hydrogenation of the present invention is carried out in the presence of molecular hydrogen, then a hydrogen pressure of 0.1-20, preferably 0.2-10 and particularly preferably between 1-8 MPa should be adjusted.

The transfer hydrogenation of the present invention is carried out in the presence of a hydrogen donor, such as formic acid or a salt thereof, or 2-propanol or other alcohols having a hydrogen atom in α-position. Among combinations of the hydrogen donor and base, when the hydrogen donor is formic acid, it is preferable to use an amine as a base. In this case, formic acid and the amine may be added separately into the reaction system, or it is also acceptable to use a mixture of formic acid and an amine (e.g. the azeotropic mixture of formic acid and triethylamine) prepared in advance. If the hydrogen donor is a liquid it may be used as the reaction solvent or co-solvent.

The Compound of Formula IIIe

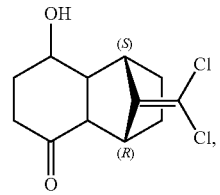

(IIIe)

and its isomers of formulae IIIf-IIIm

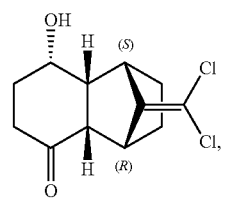

(IIIf)

-continued

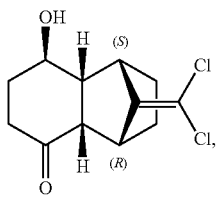
(IIIg)

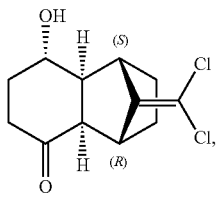
(IIIh)

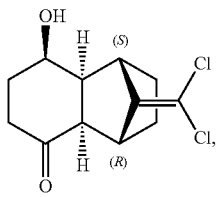
(IIIi)

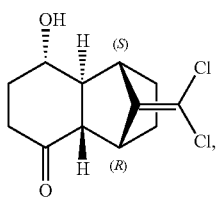
(IIIj)

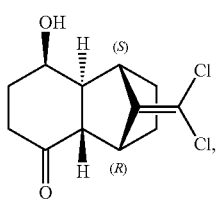
(IIIk)

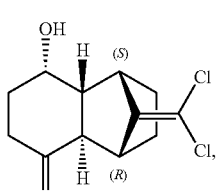
(IIIL)

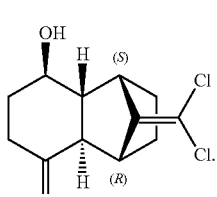
(IIIm)

are novel and especially developed for the process according to the invention and therefore constitute a further object of the invention.

In a preferred embodiment of the present invention the enantioselective reduction of the compound of formula II is done via hydrogenation in presence of a transition metal catalyst, preferably a ruthenium catalyst.

In another preferred embodiment of the present invention the enantioselective reduction of the compound of formula II is done via transfer hydrogenation in presence of a transition metal catalyst, preferably a ruthenium catalyst.

In an especially preferred embodiment of the present invention the enantioselective reagent is chloro{(R)-(+)-2,2'-bis[di(3,5-xylyl)phosphino]-1,1'-binaphthyl}[(2R)-(−)-1-(4-methoxyphenyl)-1'-(4-methoxyphenyl-kC)-3-methyl-1,2-butanediamine]ruthenium(II).

Reaction step b) can be performed as described in WO 2011/015416. Suitable acids for reaction step b) are strong acids like phosphoric acid, polyphosphoric acids, concentrated $H_2SO_4$, methanesulfonic acid, p-toluenesulfonic acid, immobilized acids (fixed on polymeric carriers) e.g. like Amberlyst™, preferably concentrated $H_2SO_4$. Dependent on the used acid, the reaction can be performed at temperatures from 10° C. to 150° C. A preferred temperature range for the use of concentrated $H_2SO_4$ as solvent is from 10 to 25° C. For concentrated $H_2SO_4$, the weight ratio of starting material to the concentrated $H_2SO_4$ is from 1:0.2 to 1:10, preferably 1:1 or less in which case a solvent is required and the preferred temperature range is 70-90° C. The compound of formula IVa is added to the acid in solid form or the acid is added to a solution of compound of formula IVa in an organic solvent. The reaction can be supported by azeotropic distillation of water, optionally under reduced pressure, especially if a catalytic amount of acid is used.

Suitable organic solvents for reaction step b) are for example toluene, xylene, methyl cyclohexane, chlorobenzene or dichlorobenzene, preferably toluene. As any elimination, this reaction can be done by converting the hydroxyl to a suitable leaving group such as for example halogen (Br, Cl, by reaction for example with $PCl_5$, $PBr_3$, $SOCl_2$) or sulfonate (by reaction for example with methansulfonylchloride in presence of base) or acetate followed by treatment with a base, acid or lewis acid (for example KOH, NaOH NaO$^t$Bu, KO$^t$Bu or tertiary amines including aromatic such as for example pyridine).

The Compound of Formula IVa

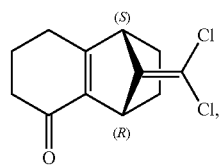
(IVa)

can occur in the following isomers or mixtures thereof:

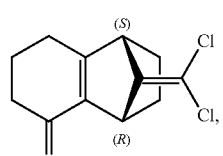
(IVa)

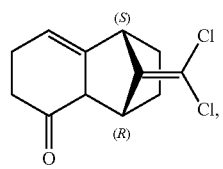
(IVb)

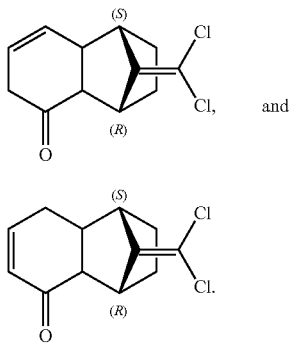

(IVc)

(IVd)

and

The isolation or purification of a specific isomer or a isomer mixture of formula IVa is not necessary. The compound of formula IVa and its isomers are novel and especially developed for the process according to the invention and therefore constitute a further object of the invention.

Reaction step c) can be performed as described in WO 2011/015416. Hydroxylamine can be used as free base in water (50% solution is commercially available) or generated in situ from its salts such as for example hydrochloride or sulfate by treatment with a base (for example triethylamine, pyridine, NaOH or KOH, sodium acetate, potassium or sodium carbonate). Hydroxylamine is preferably used in form of its sulfate or hydrochloride and in an amount of 1 to 2 equivalents, in particular 1.1 to 1.3 equivalents with regard to the compound of formula IVa. Suitable bases for this reaction step are for example pyridine, tertiary amines like triethylamine, NaOH or KOH, sodium acetate, potassium or sodium carbonate Especially preferred is sodium acetate and NaOH. The base is used in an amount of 1 to 2 equivalents, preferably 1-1.5 equivalents with regard to the compound of formula IVa. Suitable solvents are alcohols (preferred anhydrous), dimethylformamide, N-methyl-2-pyrrolidone, or $CH_3CN$, in particular anhydrous ethanol or anhydrous methanol. An especially preferred solvent is anhydrous ethanol. Reaction step e) can be advantageously performed at temperatures of from 10 to 40° C. preferably at 25° C. or ambient temperature. The reaction can be also performed in a two phase system (organic solvent/water, organic solvent for example are: toluene, xylene, methylcyclohexane) at temperatures of from 50-100° C. using the above mentioned hydroxylamine sources and bases in the presence of phase transfer catalysts selected from carboxylic acids (for example acetic, propionic, isobutyric, pivalic, valeric, isovaleric, benzoic, 2-ethylhexanoic) used in amount 2-50 mol %. A preferred amount of catalyst is 5-10 mol %, a preferred temperature is 80-90° C., preferred catalysts are benzoic acid and 2-ethylhexanoic acid.

With sodium acetate as base, a phase transfer catalyst is not required. This is a preferred embodiment of the process.

The compound of formula Va can occur in the following isomers or mixtures thereof:

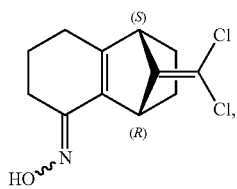

(Va)

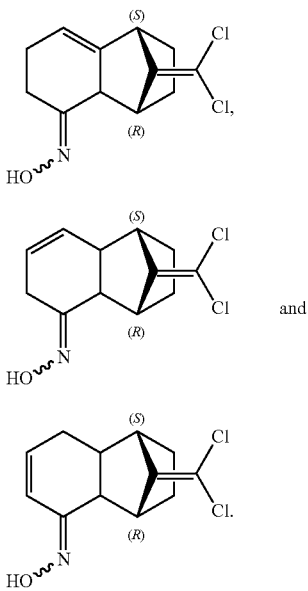

(Vb)

(Vc)

and (Vd)

The isolation or purification of a specific isomer or a isomer mixture of formula Va is not necessary. The compound of formula Va and its isomers are novel and especially developed for the process according to the invention and therefore constitute a further object of the invention.

Reaction step d) can be performed as described in WO 2011/015416 or in WO2012/101139. A preferred embodiment of reaction step d) comprises acylating the oxime oxygen of the compound of formula Va (Va)

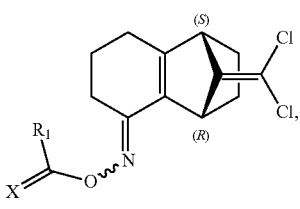

in the presence of a solvent and an acylating agent of formula XXIIa $R_1$—C(X)—Cl(XXIIa), wherein X is oxygen or sulfur, preferably oxygen; $R_1$ is $C_1$-$C_6$alkoxy, $CH_3$—C(=$CH_2$)—O—, phenoxy or trichloromethoxy; preferably $C_1$-$C_6$alkoxy, phenoxy or trichloromethoxy; and reacting the so obtained product of formula XXIIIa (XXIIIa)

wherein X is oxygen or sulfur, preferably oxygen, $R_1$ is $C_1$-$C_6$alkoxy, $CH_3$—$C(=CH_2)$—O—, phenoxy or trichloromethoxy;

with the compound of formula VI

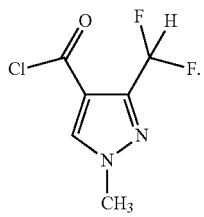

(VI)

Preferred acylating agents of formula XXIIa are those, wherein $R_1$ is methoxy, ethoxy, isopropoxy, phenoxy or isopropenyloxy and X is oxygen, more preferably $R_1$ is methoxy, ethoxy, isopropoxy or phenoxy and X is oxygen, in particular $R_1$ is ethoxy.

The compounds of formula XXIIIa are novel, were especially developed for the process according to the invention and therefore constitute a further object of the invention. Preferred compounds formula XXIIIa are those, wherein $R_1$ is methoxy, ethoxy, isopropoxy, phenoxy or isopropenyloxy and X is oxygen, more preferably $R_1$ is methoxy, ethoxy, isopropoxy or phenoxy and X is oxygen, in particular $R_1$ is ethoxy.

The process according to the invention consists of two chemical transformations: reaction of the oxime oxygen with the acylating agent followed by in situ transformation of the acylated derivative to the compound of formula Ib by reaction with 1.0 to 1.3 equivalents preferably 1.05 equivalents of the compound of formula VI advantageously in the presence of an acid (preferably HCl, $H_2SO_4$ or $CH_3SO_3H$, most preferred $CH_3SO_3H$). The addition of the acid accelerates the formation of the compound of formula Ib and therefore significantly reduces the reaction time.

The acylation is advantageously performed in the presence of a base. The base is used in an amount of 1 to 1.5 equivalents with respect to the compound of formula Va, in particular in an amount of 1.2 equivalents. Suitable bases for the acylation are pyridine or tertiary amines like triethylamine. Triethylamine is especially preferred as a base. Preferred reaction temperatures for the process are from 60 to 150° C., in particular 85-125° C., most preferably 95 to 115° C. In another preferred embodiment of the present invention the reaction is performed at a temperature from 130 to 135° C. with an acylation agent of the formula XXIIa wherein $R_1$ is ethoxy and X is oxygen.

Suitable solvents are toluene, dioxane, tetrahydrofurane, xylene, chlorobenzene or acetonitrile. Most preferred solvent is xylene.

If the acylation agent is phosgen or thiophosgen, the structure of the compound obtained from the reaction of the oxime of formula Va with phosgen or thiophosgen depends on the order of addition of the reactants.

If the compound of formula XXIIa, wherein $R_1$ is chloro and X is oxygen or sulfur is added to the compound of formula Va; the compound of formula XXIVa

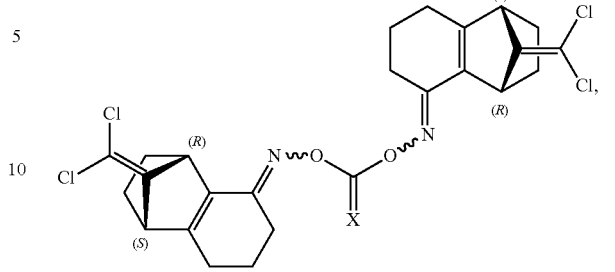

(XXIVa)

wherein X is oxygen or sulfur; is obtained.

If the compound of formula Va is added to the compound of formula XXIIa wherein $R_1$ is chloro and X is oxygen or sulfur; the compound of formula XXVa

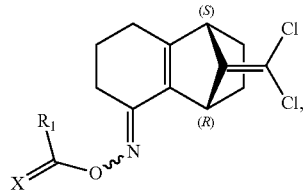

(XXVa)

wherein X is oxygen or sulfur and $R_1$ is chloro; is obtained.

For compounds of formula XXIIIa, wherein $R_1$ is $C_1$-$C_6$alkoxy, $CH_3$—$C(=CH_2)$—O—, phenoxy or trichloromethoxy if X is oxygen; the compound of formula XVIa was obtained independently from the order of addition of the reactants.

The compounds of formula XXIVa and XXVa are novel, were especially developed for the process according to the invention and therefore constitute a further object of the invention. In a preferred compound of formula XXVa, X is oxygen.

It was also found that the addition of $CH_3SO_3H$ accelerates the formation of the compound of formula Ib and therefore significantly reduces the reaction time.

The compound of formula VI is known and commercially available. The compound is disclosed, for example, in U.S. Pat. No. 5,093,347.

PREPARATORY EXAMPLES

HPLC Waters Alliance 2695
UV Detector Waters 996 DAD

Example P1

Preparation of Enantiomerically Enriched (1S,4R)-9-dichloromethylene-8-hydroxy-octahydro-1,4-methano-naphthalen-5-one of Formula IIIf

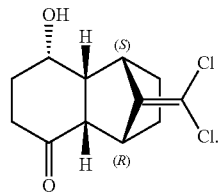

(IIIf)

In a 100 ml Hastelloy autoclave equipped with a magnetic stirring bar under argon, a mixture of the compound of formula II (1.00 g, 3.86 mmol), chloro{(R)-(+)-2,2'-bis[di(3,5-xylyl)phosphino]-1,1'-binaphthyl}[(2R)-(−)-1-(4-methoxyphenyl)-1'-(4-methoxyphenyl-kC)-3-methyl-1,2-butanediamine]ruthenium(II) ((R)-RUCY™-XylBINAP, Strem catalog 44-0217) (0.0183 g, 0.0154 mmol), dichloromethane (10.0 ml) and iso-propanol (8.0 ml) was treated with potassium tert-butoxide (0.0223 g, 0.193 mmol) dissolved in iso-propanol (2.0 ml). The autoclave was purged with 0.5 MPa hydrogen (3-times), pressurized with 5 MPa hydrogen and vigorously stirred at 25-28° C. for 22 hours. The crude reaction mixture was evaporated and the product was isolated via column chromatography (silica, heptanes→30% ethyl acetate in heptanes gradient) giving 900 mg of (1S,4R)-9-dichloromethylene-8-hydroxy-octahydro-1,4-methano-naphthalen-5-one in form of a white solid.

Chiral HPLC analysis (Chiralpack ID, 0.46 cm×25 cm, heptane:iso-propanol=90:10, 1 ml/min, Detection: 220 nm): retention time 8.83 minutes (major enantiomer, 83.4%), 12.93 minutes (minor enantiomer 16.6%). The sign of the optical rotation in CHCl$_3$ is (+).

$^1$H NMR analysis indicated that the product diastereopurity (ratio of major diastereoisomer IIIf/sum of all diastereoisomers (formulae IIIe-IIIm)) is 96%.

$^1$H NMR (CDCl$_3$, 400 MHz) δ (major isomer) 1.58-1.72 (m, 3H), 1.84 (bs, 1H), 2.04 (m, 2H), 2.20-2.35 (m, 2H), 2.48-2.55 (m, 1H), 2.74 (m, 2H), 3.12 (m, 1H), 3.28 (m, 1H), 4.41 (m, 1H).

Example P2

Preparation of the Enantiomerically Enriched Compound of Formula IVa

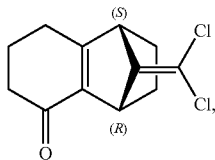

(IVa)

Finely powdered compound of formula IIIf (0.50 g, 1.915 mmol) was added to an intensively stirred 96% sulphuric acid (2.5 ml) at 0° C. The reaction mixture was stirred 10 min at the same temperature and at ambient temperature for 1 hour (orange solution). The reaction mixture was poured into water and extracted with dichloromethane. The organic phase was dried over Na$_2$SO$_4$ and evaporated in vacuum giving 417 mg of brown solid.

Chiral HPLC analysis (Chiralpack ID, 0.46 cm×25 cm, heptane:iso-propanol=90:10, 1 ml/min, Detection: 240 nm): retention time 7.61 minutes (minor enantiomer, 14.5%), 8.16 minutes (major enantiomer, 85.5%).

$^1$H NMR (CDCl$_3$, 400 MHz) δ 1.23-1.32 (m, 2H), 1.88-2.14 (m, 4H), 2.23-2.30 (m, 1H), 2.35-2.57 (m, 3H), 3.49 (m, 1H), 3.87 (m, 1H).

Example P3

Preparation of Enantiomerically Enriched Compound of Formula Va

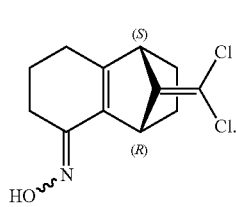

(Va)

A mixture of compound of formula IVa (0.385 g, 1.584 mmol), hydroxylamine hydrochloride (0.132 g, 1.900 mmol), pyridine (0.1879 g, 2.376 mmol) and absolute ethanol (3.0 ml) was stirred at ambient temperature for 4.5 hours. Water was added to the reaction mixture and the solid formed was filtered and dried giving 313 mg of the desired product.

$^1$H-NMR (CDCl$_3$, 400 MHz,): δ 1.36-1.26 (m, 2H); 2.03-1.78 (m, 4H); 2.27-2.17 (m, 1H); 2.49-2.33 (m, 2H); 2.78-2.68 (m, 1H); 3.40 (d, 1H, J=2.6 Hz); 3.80 (d, 1H, J=3.3 Hz);

Example P4

Preparation of Enantiomerically Enriched 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide of Formula Ib

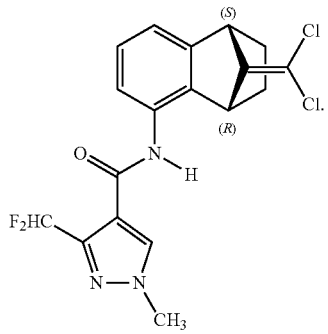

(Ib)

To a stirred solution of the compound of formula Va (0.100 g, 0.3874 mmol) in dioxane (0.5 mL) was added triethylamine (0.0392 g, 0.3874 mmol) and then 4-(difluoromethyl)-1-methyl-pyrazole-3-carbonyl chloride (0.1508 g, 0.775 mmol) slowly. The reaction mixture was heated slowly to a temperature of 82° and kept at this temperature for 3 hours and at ambient temperature for 18 hours. After cooling to ambient temperature most of the solvent was removed by rotary evaporation and the residue was stirred with diethyl ether and water. A solution of NaOH (48 mg) in water (0.2 ml) was added and the mixture was stirred for additional 10 min. The water phase was separated and the organic phase was extracted with 1M NaOH, 1M HCl, water, dried over Na$_2$SO$_4$ and evaporated in vacuum. The crude product was purified via column chromatography (silica, heptanes/ethyl acetate 2:1→1:1) giving 75 mg of the desired product as a yellow solid.

Chiral HPLC analysis (Chiralpack ID, 0.46 cm×25 cm, heptane:iso-propanol=90:10, 1 ml/min, Detection: 260 nm): retention time 10.04 minutes (major enantiomer, 85.4%), 14.14 minutes (minor enantiomer, 14.6%). The sign of the optical rotation in CHCl$_3$ is (−).

$^1$H NMR (CDCl$_3$, 400 MHz) δ 1.37 (m, 1H), 1.49 (m, 1H), 2.09 (m, 2H), 3.90 (s, 3H), 3.94 (m, 1H), 4.07 (m, 1H), 6.91 (t, J$_{H-F}$=54.2 Hz, 1H), 7.02 (d, J=7.3 Hz, 1H), 7.16 (t, J=7.8 Hz, 1H), 7.79 (d, J=8.2 Hz, 1H), 8.01 (s, 1H), 8.15 (m, 1H).

Example P5

Preparation of the Single Enantiomer of (1S,4R)-9-dichloromethylene-8-hydroxy-octahydro-1,4-methano-naphthalen-5-one of Formula IIIf

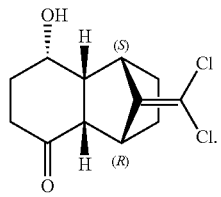

(IIIf)

A 500 ml Hastelloy autoclave was charged with compound of formula II (20.00 g, 74.9 mmol). Under argon, dry and degassed toluene (80.0 ml) was added, followed by a degassed solution of dichloro[(4S,5S)-(−)-4,5-bis(diphenylphosphinomethyl)-2,2-dimethyl-1,3-dioxolane][(S)-(+)-2-(α-methylmethanamine)-1H-benzimidazole]ruthenium (II), min. 98%, Strem catalog 44-0955 (0.05 g, 0.060 mmol) and triphenylphosphine (0.098 g, 0.375 mmol) in toluene (11.0 ml) and a solution of potassium tert-butoxide (0.433 g, 3.75 mmol) in iso-propanol (10 ml). The autoclave was purged with 0.5 MPa hydrogen (3-times), pressurized with 5 MPa hydrogen and vigorously stirred at 25-28° C. for 2 hours. The crude reaction mixture was evaporated, dissolved in ethylacetate, filtratered over a plug of silica and evaporated giving 18.32 g of (1S,4R)-9-dichloromethylene-8-hydroxy-octahydro-1,4-methano-naphthalen-5-one as a brown gum.

Chiral HPLC analysis (Chiralpack ID, 0.46 cm×25 cm, heptane:iso-propanol=90:10, 1 ml/min, Detection: 220 nm): retention time 8.83 minutes (major enantiomer, 98.9%), 12.93 minutes (minor enantiomer 1.1%). The sign of the optical rotation in CHCl$_3$ is (+).

The product was further recrystallized from toluene (35 ml) to give 15 g (77%) of IIIf as a white solid.

Chiral HPLC analysis (Chiralpack ID, 0.46 cm×25 cm, heptane:iso-propanol=90:10, 1 ml/min, Detection: 220 nm): retention time 8.83 minutes (major enantiomer, 100%), minor enantiomer not detected (<0.1%).

$^1$H NMR (CDCl$_3$, 400 MHz) δ (major isomer) 1.58-1.72 (m, 3H), 1.84 (bs, 1H), 2.04 (m, 2H), 2.20-2.35 (m, 2H), 2.48-2.55 (m, 1H), 2.74 (m, 2H), 3.12 (m, 1H), 3.28 (m, 1H), 4.41 (m, 1H).

Example P6

Preparation of the Single Enantiomer of the Compound of Formula IVa

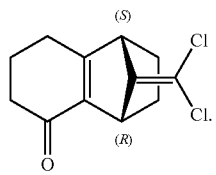

(IVa)

Finely powdered compound of formula IIIf (14 g, 53.6 mmol) was added to an intensively stirred 96% sulphuric acid (50 ml) at 0° C. The reaction mixture was stirred 10 min at the same temperature and at ambient temperature for 1 hour (orange solution). The reaction mixture was poured into ice/water and extracted with tert-butyl methyl ether. The organic phase was dried over Na$_2$SO$_4$ and evaporated in vacuum giving 12.7 g (84%) of the title compound as a brown solid Chiral HPLC analysis (Chiralpack ID, 0.46 cm×25 cm, heptane:iso-propanol=90:10, 1 ml/min, Detection: 240 nm): retention time 7.61 minutes (major enantiomer, 100%), minor enantiomer not detected (<0.1%).

$^1$H NMR (CDCl$_3$, 400 MHz) δ 1.23-1.32 (m, 2H), 1.88-2.14 (m, 4H), 2.23-2.30 (m, 1H), 2.35-2.57 (m, 3H), 3.49 (m, 1H), 3.87 (m, 1H).

Example P7

Preparation of Single Enantiomer of Compound of Formula Va

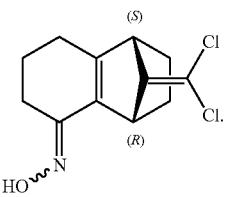

(Va)

A mixture of compound of formula IVa (10.7 g, 44.0 mmol), hydroxylamine hydrochloride (3.67 g, 52.8 mmol), pyridine (5.22 g, 66.0 mmol) and absolute ethanol (80 ml) was stirred at ambient temperature for 3.5 hours. Water/ice was added to the reaction mixture and the solid formed was filtered and dried giving 10.75 g (95% yield) of the of the title compound.

$^1$H-NMR (CDCl$_3$, 400 MHz,): δ 1.36-1.26 (m, 2H); 2.03-1.78 (m, 4H); 2.27-2.17 (m, 1H); 2.49-2.33 (m, 2H); 2.78-2.68 (m, 1H); 3.40 (d, 1H, J=2.6 Hz); 3.80 (d, 1H, J=3.3 Hz);

Example P8

Preparation of the Single Enantiomer of 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide of Formula Ib

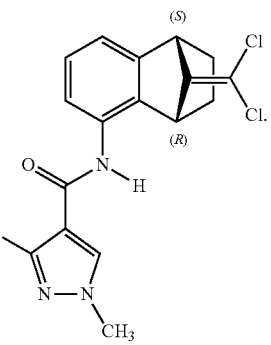

(Ib)

To a stirred solution of the compound of formula Va (10.7 g, 41.5 mmol) in dioxane (50 mL) was added triethyl amine (4.20 g, 41.5 mmol) and then 4-(difluoromethyl)-1-methyl-pyrazole-3-carbonyl chloride (16.1 g, 82.9 mmol) slowly. The reaction mixture was heated slowly to a temperature of 82° and kept at this temperature for 3 hours. After cooling to ambient temperature most of the solvent was removed by rotary evaporation and the residue was stirred with diethyl ether and water. A solution of NaOH (4.8 g) in water (20 ml) was added and the mixture was stirred for additional 30 min. The water phase was separated and the organic phase was extracted with 1M NaOH, 1M HCl, water, dried over $Na_2SO_4$ and evaporated in vacuum. The crude product was purified crystallization: the product was stirred for 2 hours in a mixture of ether and pentane; then it was filtered and washed with cold ether to give 11 g (65%) of the title compound as a white solid.

Chiral HPLC analysis (Chiralpack ID, 0.46 cm×25 cm, heptane:iso-propanol=90:10, 1 ml/min, Detection: 260 nm): retention time 10.04 minutes (major enantiomer, 100%), minor enantiomer not detected (<0.1%). The sign of the optical rotation in $CHCl_3$ is (−).

$^1$H NMR ($CDCl_3$, 400 MHz) δ 1.37 (m, 1H), 1.49 (m, 1H), 2.09 (m, 2H), 3.90 (s, 3H), 3.94 (m, 1H), 4.07 (m, 1H), 6.91 (t, $J_{H-F}$=54.2 Hz, 1H), 7.02 (d, J=7.3 Hz, 1H), 7.16 (t, J=7.8 Hz, 1H), 7.79 (d, J=8.2 Hz, 1H), 8.01 (s, 1H), 8.15 (m, 1H).

Mp=146° C.

Example P9

Enantioselective Reduction of the Compound of Formula II Via Hydrogenation

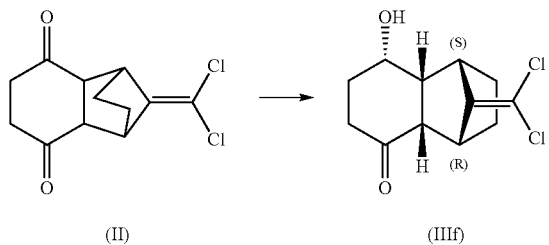

A mixture of the compound of formula II (0.1 g-4.00 g), catalyst, base, additive and solvent (1.3-3 mL/mmol) was added into a 100 ml hastelloy autoclave equipped with a magnetic stirring bar under argon. The autoclave was purged with 0.5 MPa hydrogen (3-times), pressurized with hydrogen and vigorously stirred under the conditions specified in the table below. The crude reaction mixture was evaporated and the crude product was analysed.

Chiral HPLC analysis (Chiralpack ID, 0.46 cm×25 cm, heptane:iso-propanol=90:10, 1 ml/min, Detection: 220 nm): retention time 8.83 minutes (major enantiomer), 12.93 minutes (minor enantiomer). The sign of the optical rotation for the major enantiomer in $CHCl_3$ is (+).

Conversion and selectivity (ratio of major diastereoisomer/sum of all diastereoisomers and by-products) was determined by $^1$H NMR analysis.

| Catalyst | Conditions | Conversion/ Selectivity | Ration of major: minor enantiomer |
|---|---|---|---|
| (R)-RUCY ™-XylBINAP (0.4 mol %) | 50 bar $H_2$, RT/20 h, KOtBu (0.05), IPA/DCM (1:1), 1 g scale | 100%/96% | 83:17 |
| $RuCl_2$[(R)-xylbinap][(R)-daipen (1 mol %) | 50 bar $H_2$, RT/20 h, KOtBu (0.05), IPA/TOL (1:1), 1 g scale | 75%/100% | 84:16 |
| $RuCl_2$[(R)-xylbinap][(R,R)-dpen (1 mol %) | 50 bar $H_2$, RT/3 h, KOtBu (0.1), IPA/DCM (1:1), 100 mg scale | 100%/87% | 69:33 |
| $RuCl_2$[(R)-xyl-P-Phos][(R)-iphan](1 mol %) | 10 bar $H_2$, RT/22 h, KOtBu (0.05), IPA/TOL (1:1), 100 mg scale | 100%/87% | 94:6 |
| $RuCl_2$[(S,S)-DIOP](S)-Me-BIMAH (1 mol %) | 10 bar H2, RT/18 h, KOtBu (0.05), TOL/tBuOH (9:1), 250 mg scale | 100%/98% | 96:4 |
| $RuCl_2$[(S,S)-DIOP](S)-Me-BIMAH (0.5 mol %) | 50 bar H2, RT/1 h, KOtBu (0.05), $PPh_3$ (1.5 mol %), TOL/tBuOH (9:1), 500 mg scale | 98%/98% | 97:3 |
| $RuCl_2$[(S,S)-DIOP](S)-Me-BIMAH (0.1 mol %) | 50 bar H2, RT/1 h, KOtBu (0.05), $PPh_3$ (0.5 mol %), TOL/tBuOH (9:1), 2 g scale | 97%/98% | 97:3 |
| $RuCl_2$[(S,S)-DIOP](S)-Me-BIMAH (0.05 mol %) | 50 bar H2, RT/16 h, KOtBu (0.05), $PPh_3$ (0.5 mol %), TOL/tBuOH (9:1), 4 g scale | 100%/93% | 98:2 |

IPA = 2-propanol,
DCM = dichloromethane,
TOL = toluene

RuCl2[(R)-xylbinap][(R,R)-dpen], CAS=[220114-38-5]

RuCl2[(R)-xylbinap][(R)-daipen], CAS=[220114-32-9]

(R)-RUCY™-XylBINAP (STREM catalogue Nr.=44-0217)

Chloro{(R)-(+)-2,2'-bis[di(3,5-xylyl)phosphino]-1,1'-bi-naphthyl}[(2R)-(−)-1-(4-methoxyphenyl)-1'-(4-methoxyphenyl-kC)-3-methyl-1,2-butanediamine]ruthenium(II)

$RuCl_2$[(R)-xylbinap][(R,R)-dpen, CAS=[220114-38-5]

$RuCl_2$[(R)-xyl-P-Phos][(R)-iphan], CAS=[832117-89-2]

$RuCl_2$[(S,S)-DIOP](S)-Me-BIMAH (STREM catalogue Nr.=44-0955)

Dichloro[(4S,5S)-(+)-4,5-bis(diphenylphosphinomethyl)-2,2-dimethyl-1,3-dioxolane][(S)-(+2-(α-methylmethanamine)-1H-benzimidazole]ruthenium(II).

Example P10

Enantioselective Reduction of the Compound of Formula II Via Transfer Hydrogenation

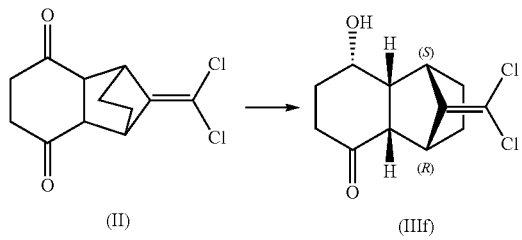

A mixture of the compound of formula II (0.25 g), catalyst (1 mol %) was vigorously stirred under the conditions specified in the table below. The crude reaction mixture was evaporated and the crude product was analysed. Conversion and selectivity (ratio of major diastereoisomer/sum of all diastereoisomers and by-products) was determined by $^1$H NMR analysis.

Chiral HPLC analysis (Chiralpack ID, 0.46 cm×25 cm, heptane:iso-propanol=90:10, 1 ml/min, Detection: 220 nm): retention time 8.83 minutes (major enantiomer), 12.93 minutes (minor enantiomer). The sign of the optical rotation for the major enantiomer in CHCl$_3$ is (+).

| Catalyst | Conditions | Conversion/Selectivity | Ration of major: minor enantiomer |
|---|---|---|---|
| (S,S)-TsDPEN—Ru-(p-cymene)-Cl (1 mol %) | KOtBu (0.025), IPA (0.2M), 60° C./20 h | 100%/71% | 67:33 |
| (S,S)-Ts-DENEB ™ (1 mol %) | KOtBu (0.025), IPA (0.2M), 40° C./20 h | 96%/97% | 77:23 |
| (S,S)-Ts-DENEB ™ (1 mol %) | HCOOH (2.0), Et3N (1.7), acetonitrile (8 mL), 0° C. to RT/16 h | 99%/99% | 92:8 |

(S,S)-TsDPEN-Ru-(p-cymene)-Cl, CAS=[192139-90-5]
(S,S)-Ts-DENEB™, CAS=[1384974-37-1]

What is claimed is:

1. A process for the enantioselective preparation of 3-difluoromethyl-1-methyl-1H-pyrazole-4-carboxylic acid ((1S,4R)-9-dichloromethylene-1,2,3,4-tetrahydro-1,4-methanonaphthalen-5-yl)-amide of formula Ib

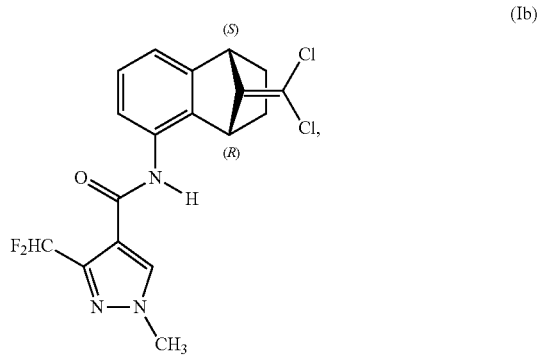

which process comprises
a) reducing a compound of formula II

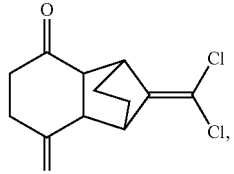

with an enantioselective reagent to a compound of formula IIIe

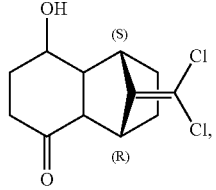

b) dehydrating the compound of formula IIIe in the presence of an acid to the compound of formula IVa

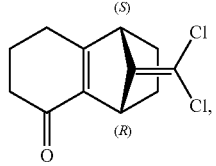

c) reacting the compound of formula IVa with hydroxylamine to the compound of formula Va

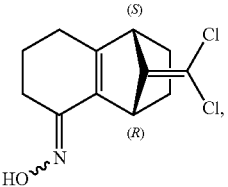

and
d) acylating the oxime oxygen of the compound of formula Va in the presence of a solvent and an acylating agent and finally reacting the obtained product with the compound of formula VI

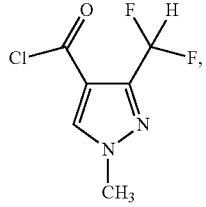

or e) reacting the compound of formula V with an excess of the compound of formula VI.

2. A process according to claim 1, wherein the enantioselective reduction of the compound of formula II is done via hydrogenation in the presence of a transition metal catalyst.

3. A process according to claim 1, wherein the enantioselective reduction of the compound of formula II is done via transfer hydrogenation in the presence of a transition metal catalyst.

4. A process according to claim 1, wherein the enantioselective reagent is a ruthenium catalyst.

5. A process according to claim 2, wherein the enantioselective reagent is a ruthenium catalyst.

6. A process according to claim 3, wherein the enantioselective reagent is a ruthenium catalyst.

7. A process according to claim 1, wherein the enantioselective reagent is chloro{(R)-(+)-2,2'-bis[di(3,5-xylyl)phosphino]-1,1'-binaphthyl}[(2R)-(+)1-(4-methoxyphenyl) -1'-(4-methoxyphenyl-kC)-3-methyl-1,2-butanediamine]ruthenium(II).

8. A process according to claim 1, wherein the enantioselective reagent is dichloro[(4S,5S)-(+)-4,5-bis(diphenylphosphinomethyl)-2,2-dimethyl-1,3-dioxolane ][(S)-(–)-2-(α-methylmethanamine)-1 H-benzimidazole]ruthenium (II).

9. The compound (1S,4R)-9-dichloromethylene-8-hydroxy-octahydro-1,4-methano-naphthalen-5-one of formula IIIe

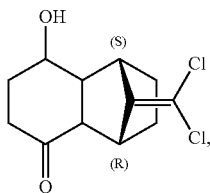

(IIIe)

or a spatial isomer thereof.

10. The compound (1S,4R)-9-dichloromethylene-2,3,4,6,7,8-hexahydro-1 H-1,4-methano-naphthalen-5-one of formula

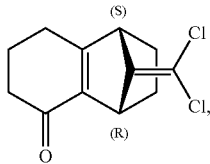

(IVa)

or a spatial isomer thereof.

11. The compound (1 S,4R)-9-dichloromethylene-2,3,4,6,7,8-hexahydro-1H-1,4-methano-naphthalen-5-one oxime of formula Va

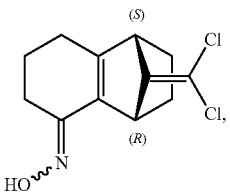

(Va)

or a spatial isomer thereof.

12. A compound of formula XXIIIa

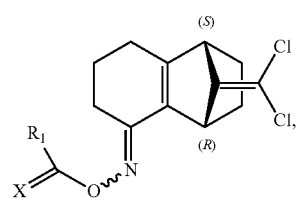

(XXIIIa)

wherein X is oxygen or sulfur, $R_1$ is $C_1$-$C_6$alkoxy, $CH_3$—C($=CH_2$)—O —, phenoxy or trichloromethoxy; or a spatial isomer thereof.

13. A compound of formula XXIVa

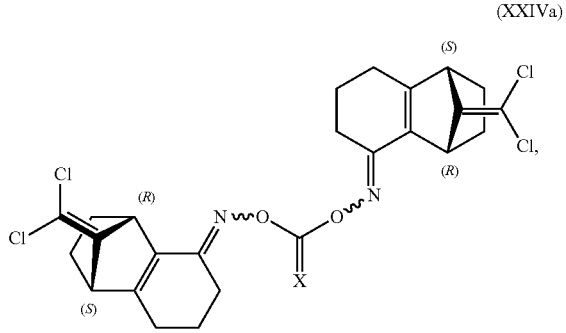

(XXIVa)

wherein X is oxygen or sulfur, or a spatial isomer thereof.

* * * * *